US009396309B2

(12) United States Patent
Watanabe et al.

(10) Patent No.: US 9,396,309 B2
(45) Date of Patent: Jul. 19, 2016

(54) DISPLAY APPARATUS AND DISPLAY METHOD DISPLAYING SIMULATION RESULTS OF A THREE DIMENSIONAL MODEL OF AN ORGAN

(71) Applicants: FUJITSU LIMITED, Kawasaki-shi, Kanagawa (JP); The University of Tokyo, Tokyo (JP)

(72) Inventors: Masahiro Watanabe, Kawswaki (JP); Satoshi Fuchikami, Fukuoka (JP); Yoshimasa Kadooka, Kawasaki (JP); Toshiaki Hisada, Tokyo (JP); Seiryo Sugiura, Tokyo (JP); Takumi Washio, Tokyo (JP); Jun-ichi Okada, Tokyo (JP)

(73) Assignees: FUJITSU LIMITED, Kawasaki (JP); THE UNIVERSITY OF TOKYO, Tokyo (JP)

( * ) Notice: Subject to any disclaimer, the term of this patent is extended or adjusted under 35 U.S.C. 154(b) by 483 days.

(21) Appl. No.: 13/912,806

(22) Filed: Jun. 7, 2013

(65) Prior Publication Data

US 2013/0332134 A1 Dec. 12, 2013

(30) Foreign Application Priority Data

Jun. 8, 2012 (JP) ................................ 2012-131244

(51) Int. Cl.
*G06F 19/00* (2011.01)
*G06T 17/00* (2006.01)

(52) U.S. Cl.
CPC .................................. *G06F 19/3437* (2013.01)

(58) Field of Classification Search
USPC .................................................. 345/419–427
See application file for complete search history.

(56) References Cited

U.S. PATENT DOCUMENTS 5,947,899 A * 9/1999 Winslow .................. A61B 5/00 128/920
2011/0292031 A1* 12/2011 Zhu ......................... G06T 19/20 345/419
2011/0292039 A1* 12/2011 Watanabe ............... G06T 15/50 345/419
2013/0332126 A1* 12/2013 Watanabe ............. G06F 19/321 703/6

OTHER PUBLICATIONS

N Smith, et al., euHeart: Personalized and Integrated Cardiac Care Using Patient-Specific Cardiovascular Modelling, 2011, Interface Focus, pp. 1-16, DOI: 10.1098/rsfs.2010.0048.*

(Continued)

*Primary Examiner* — Michael J Cobb
(74) *Attorney, Agent, or Firm* — Staas & Halsey LLP

(57) ABSTRACT

A display method displaying simulation results of a three dimensional simulation model of an internal organ by detecting a first element string along a first line that passes through the simulation model from a first element group having physical values according to a simulation model position of a first unit time; extracting first physical values of the first element string from the first element string; setting a second line that passes through the simulation model of a second unit time subsequent to the first unit time; detecting a second element string along the second line and corresponding to the first element string from a second element group having physical values according to a simulation model position of the second unit time; extracting second physical values of the second element string from the second element string; and displaying the first physical values and the second physical values.

11 Claims, 13 Drawing Sheets

L
Lpi
a b c d e f
LEi
M(ti)

(56) References Cited

OTHER PUBLICATIONS

H Baek, MV Jayaraman, PD Richardsonm, GE Karniadakis, Flow Instability and Wall Shear Stress Variation in Intracranial Aneurysms, 2010, Journal of The Royal Society Interface, 7:967-988, DOI:10.1098/rsif.2009.0476.*

KitwarePublic, ParaView User's Guide (v. 3.10), 2011, retrieved from <<www.rasmsys.com/resources/Documents/ParaView-Documentation/ParaViewUsersGuide.pdf>>, accessed Oct. 16, 2015.*

A Hosoi, T Washio, J Okada, Y Kadooka, K Nakajima, T Hisada, A Multi-Scale Heart Simulation on Massively Parallel Computers, 2010, 2010 International Conference for High Performance Computing, Networking, Storage and Analysis, pp. 1-11 DOI:10.1109/SC.2010.5.*

K Hirota, J Okada, T Washio, T Hisada, S Sugiura Short Paper: Echocardiography Simulator based on Computer-Simulated Heart, 2009, Joint Virtual Reality Conference of EGVE—ICAT—EuroVR, pp. 73-76, DOI: 10.2312/EGVE/JVRC09/073-076.*

KitwarePublic, "ParaView /Users Guide/Plotting and Probing Data," (Mar. 2012), pp. 1-3, www.itk/Wiki/ParaView/Users_Guide/Plotting_and_Probing_Data.

* cited by examiner

TIME t1

TIME t2

200
CPU
201
ROM
202
RAM
203
MAGNETIC DISK DRIVE
204
MAGNETIC DISK
205
OPTICAL DISK DRIVE
206
OPTICAL DISK
207
DISPLAY
208
I/F
209
210
KEYPAD
211
MOUSE
212
SCANNER
213
PRINTER
214
NETWORK

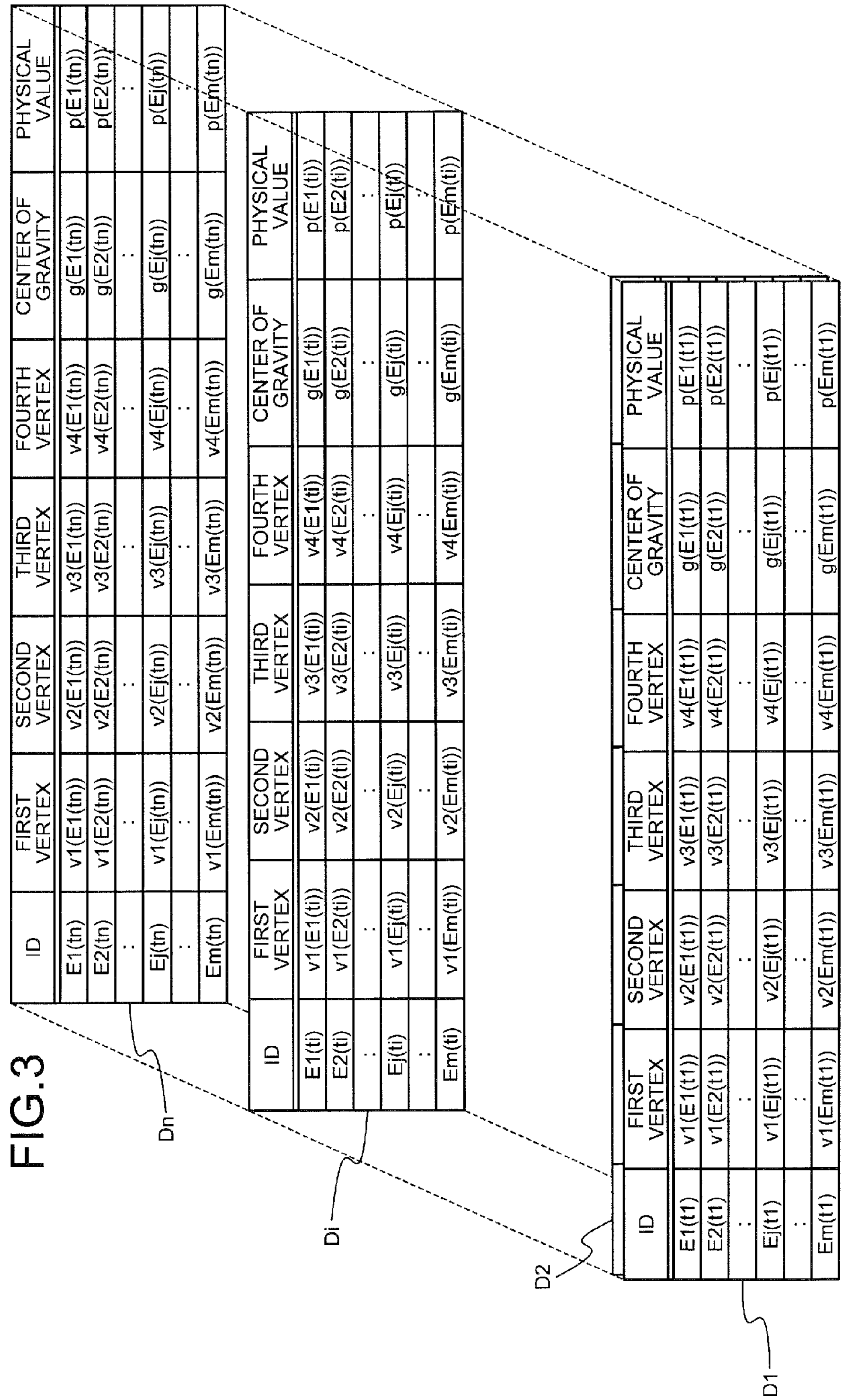
FIG.3
ID
FIRST VERTEX
SECOND VERTEX
THIRD VERTEX
FOURTH VERTEX
CENTER OF GRAVITY
PHYSICAL VALUE
E1(tn) v1(E1(tn)) v2(E1(tn)) v3(E1(tn)) v4(E1(tn)) g(E1(tn)) p(E1(tn))
E2(tn) v1(E2(tn)) v2(E2(tn)) v3(E2(tn)) v4(E2(tn)) g(E2(tn)) p(E2(tn))
Ej(tn) v1(Ej(tn)) v2(Ej(tn)) v3(Ej(tn)) v4(Ej(tn)) g(Ej(tn)) p(Ej(tn))
Em(tn) v1(Em(tn)) v2(Em(tn)) v3(Em(tn)) v4(Em(tn)) g(Em(tn)) p(Em(tn))
E1(ti) v1(E1(ti)) v2(E1(ti)) v3(E1(ti)) v4(E1(ti)) g(E1(ti)) p(E1(ti))
E2(ti) v1(E2(ti)) v2(E2(ti)) v3(E2(ti)) v4(E2(ti)) g(E2(ti)) p(E2(ti))
Ej(ti) v1(Ej(ti)) v2(Ej(ti)) v3(Ej(ti)) v4(Ej(ti)) g(Ej(ti)) p(Ej(ti))
Em(ti) v1(Em(ti)) v2(Em(ti)) v3(Em(ti)) v4(Em(ti)) g(Em(ti)) p(Em(ti))
E1(t1) v1(E1(t1)) v2(E1(t1)) v3(E1(t1)) v4(E1(t1)) g(E1(t1)) p(E1(t1))
E2(t1) v1(E2(t1)) v2(E2(t1)) v3(E2(t1)) v4(E2(t1)) g(E2(t1)) p(E2(t1))
Ej(t1) v1(Ej(t1)) v2(Ej(t1)) v3(Ej(t1)) v4(Ej(t1)) g(Ej(t1)) p(Ej(t1))
Em(t1) v1(Em(t1)) v2(Em(t1)) v3(Em(t1)) v4(Em(t1)) g(Em(t1)) p(Em(t1))
Dn
Di
D2
D1

FIG.6

| TIME | TETRA ELEMENT STRING | | | | | |
|---|---|---|---|---|---|---|
| t1 | E1(t1) | E2(t1) | E3(t1) | E8(t1) | ... | E50(t1) |
| t2 | E1(t2) | E4(t2) | E5(t2) | E6(t2) | ... | E50(t2) |
| : | : | : | : | : | : | : |
| tn | E1(tn) | E3(tn) | E9(tn) | E15(tn) | ... | E50(tn) |

FIG.7

| TIME | INTER-ELEMENT DISTANCE | | | |
|---|---|---|---|---|
| t1 | d(E1,E2)t1 | d(E2,E3)t1 | d(E3,E8)t1 | ... |
| t2 | d(E1,E4)t2 | d(E4,E5)t2 | d(E5,E6)t2 | ... |
| : | : | : | : | : |
| tn | d(E1,E3)tn | d(E3,E9)tn | d(E9,E15)tn | ... |

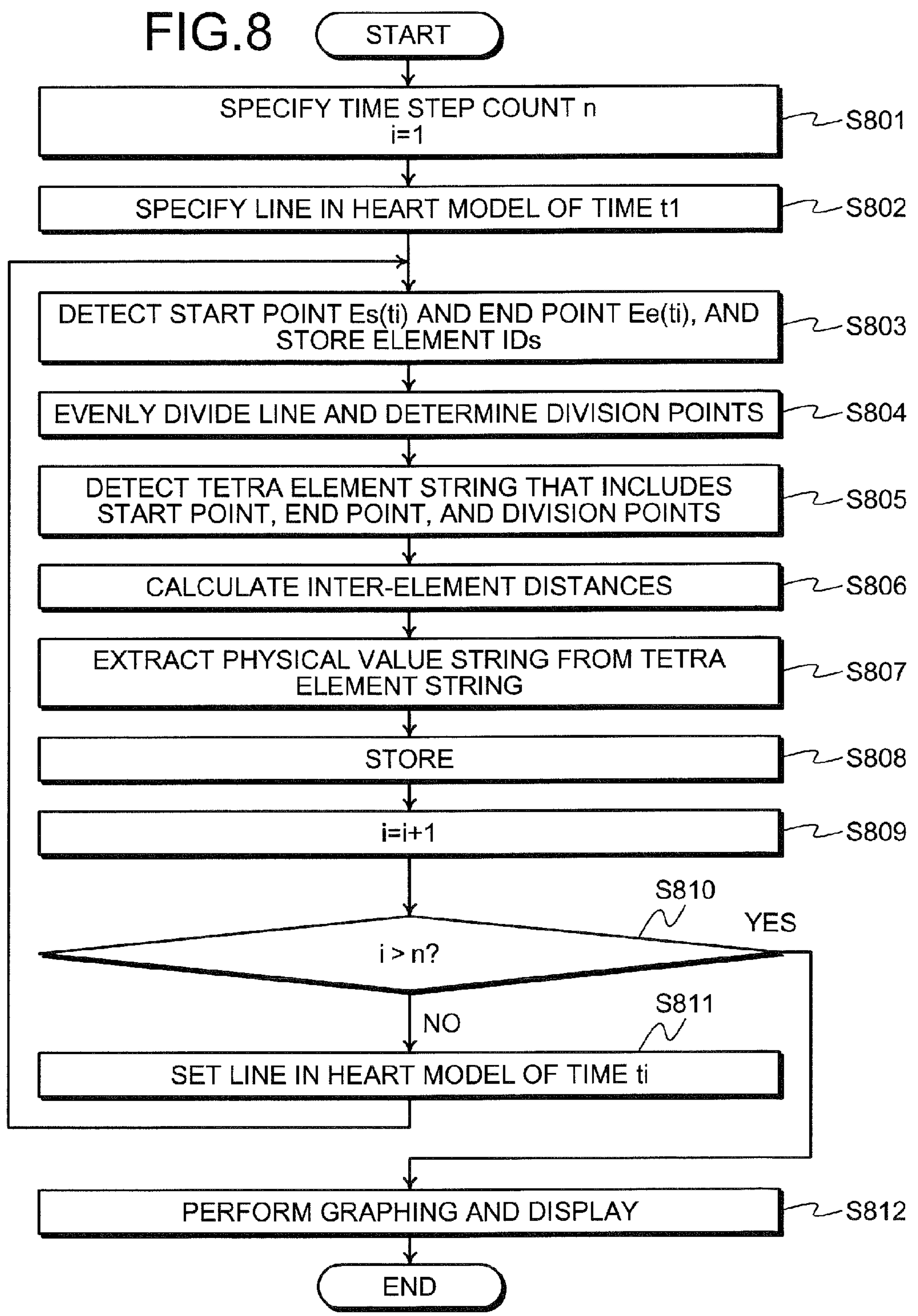
FIG.8
START
SPECIFY TIME STEP COUNT n
i=1
S801
SPECIFY LINE IN HEART MODEL OF TIME t1
S802
DETECT START POINT Es(ti) AND END POINT Ee(ti), AND STORE ELEMENT IDs
S803
EVENLY DIVIDE LINE AND DETERMINE DIVISION POINTS
S804
DETECT TETRA ELEMENT STRING THAT INCLUDES START POINT, END POINT, AND DIVISION POINTS
S805
CALCULATE INTER-ELEMENT DISTANCES
S806
EXTRACT PHYSICAL VALUE STRING FROM TETRA ELEMENT STRING
S807
STORE
S808
i=i+1
S809
S810
YES
i > n?
NO
S811
SET LINE IN HEART MODEL OF TIME ti
PERFORM GRAPHING AND DISPLAY
S812
END

FIG.10

| TIME | TETRA ELEMENT STRING | | | | | |
|---|---|---|---|---|---|---|
| t1 | E1(t1) | E2(t1) | E3(t1) | E8(t1) | ... | E50(t1) |
| t2 | E3(t2) | E4(t2) | E8(t2) | E10(t2) | ... | E62(t2) |
| : | : | : | : | : | : | : |
| tn | E2(tn) | E3(tn) | E9(tn) | E15(tn) | ... | E78(tn) |

FIG.11

| TIME | INTER-ELEMENT DISTANCE | | | |
|---|---|---|---|---|
| t1 | d(E1,E2)t1 | d(E2,E3)t1 | d(E3,E8)t1 | ... |
| t2 | d(E3,E4)t2 | d(E4,E8)t2 | d(E8,E10)t2 | ... |
| : | : | : | : | : |
| tn | d(E2,E3)tn | d(E3,E9)tn | d(E9,E15)tn | ... |

START
SPECIFY TIME STEP COUNT n
S1201
SPECIFY LINE IN HEART MODEL OF TIME t1
S1202
i=1
S1203
DETECT TETRA ELEMENT STRING THAT PASSES THROUGH LINE
S1204
CALCULATE INTER-ELEMENT DISTANCES
S1205
EXTRACT PHYSICAL VALUE STRING FROM TETRA ELEMENT STRING
S1206
STORE
S1207
i=i+1
S1208
S1209
i > n?
YES
NO
S1210
SET LINE IN HEART MODEL OF TIME ti
PERFORM GRAPHING AND DISPLAY
S1211
END

FIG.14

| TIME | TETRA ELEMENT STRING | | | | | |
|---|---|---|---|---|---|---|
| t1 | E1(t1) | E2(t1) | E3(t1) | E4(t1) | ... | E50(t1) |
| t2 | E1(t2) | E2(t2) | E3(t2) | E4(t2) | ... | E50(t2) |
| : | : | : | : | : | : | : |
| tn | E1(tn) | E2(tn) | E3(tn) | E4(tn) | ... | E50(tn) |

FIG.15

| TIME | INTER-ELEMENT DISTANCE | | | |
|---|---|---|---|---|
| t1 | d(E1,E2)t1 | d(E2,E3)t1 | d(E3,E4)t1 | ... |
| t2 | d(E1,E2)t2 | d(E2,E3)t2 | d(E3,E4)t2 | ... |
| : | : | : | : | : |
| tn | d(E1,E2)tn | d(E2,E3)tn | d(E3,E4)tn | ... |

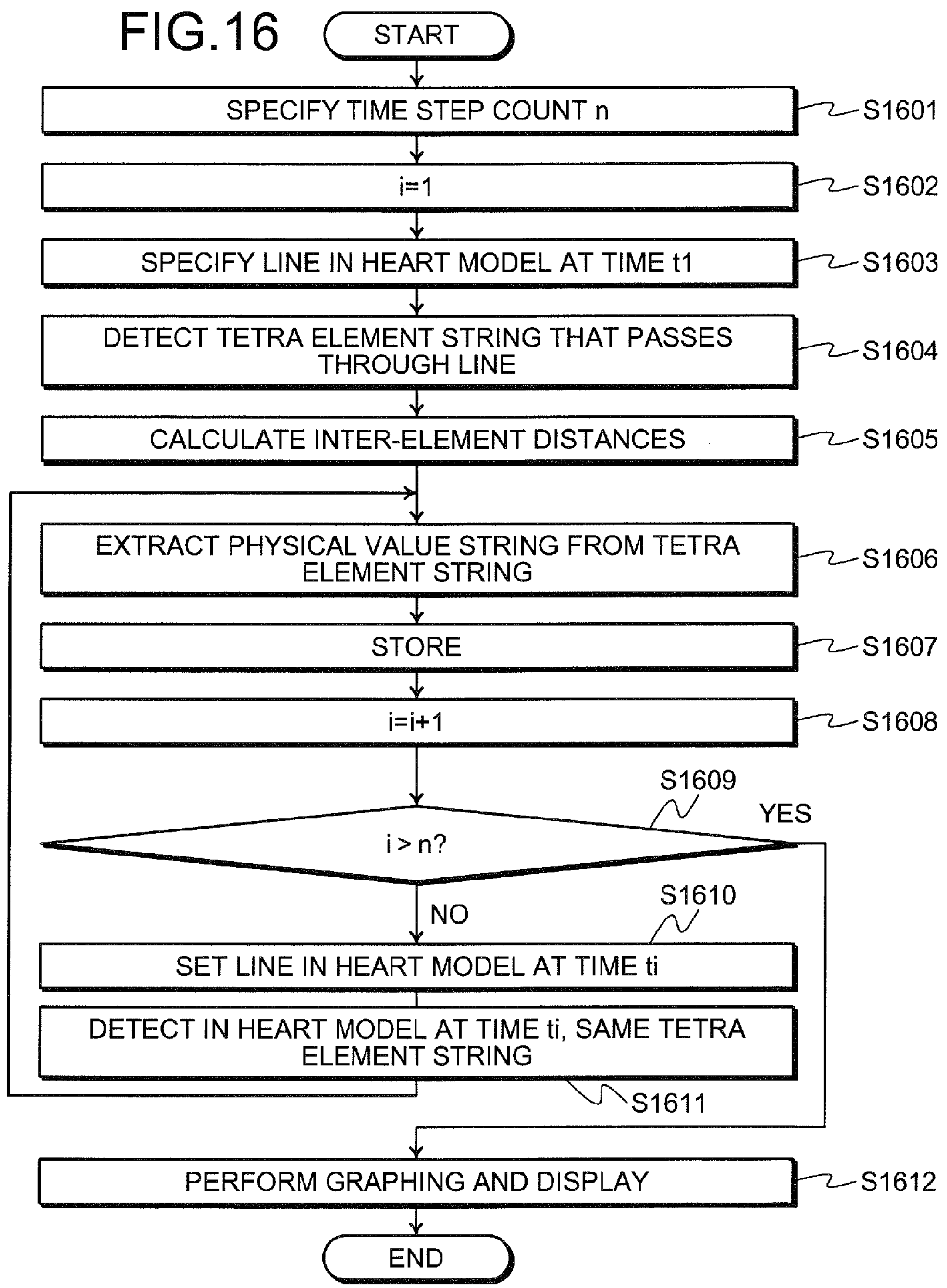
FIG.16
START
SPECIFY TIME STEP COUNT n
S1601
i=1
S1602
SPECIFY LINE IN HEART MODEL AT TIME t1
S1603
DETECT TETRA ELEMENT STRING THAT PASSES THROUGH LINE
S1604
CALCULATE INTER-ELEMENT DISTANCES
S1605
EXTRACT PHYSICAL VALUE STRING FROM TETRA ELEMENT STRING
S1606
STORE
S1607
i=i+1
S1608
S1609
i > n?
YES
NO
S1610
SET LINE IN HEART MODEL AT TIME ti
DETECT IN HEART MODEL AT TIME ti, SAME TETRA ELEMENT STRING
S1611
PERFORM GRAPHING AND DISPLAY
S1612
END

DISPLAY APPARATUS AND DISPLAY METHOD DISPLAYING SIMULATION RESULTS OF A THREE DIMENSIONAL MODEL OF AN ORGAN

CROSS REFERENCE TO RELATED APPLICATIONS

This application is based upon and claims the benefit of priority of the prior Japanese Patent Application No. 2012-131244, filed on Jun. 8, 2012, the entire contents of which are incorporated herein by reference.

FIELD

The embodiments discussed herein are related to a computer product, a display method, and a display apparatus.

BACKGROUND

Biological phenomena such as that of the heart in humans and animals where consequent to electrical signals, the myocardium of the heart contracts to pump blood to the entire body has been conventionally reproduced by numerical analysis. In general, the results of the numerical analysis are displayed using computer graphics technology to indicate distribution by color. Meanwhile, to extract a value of a portion of cardiac muscle for viewing, calculation elements having arranged physical values and values of calculation nodes have to be checked. Visualization technology for displaying partial values has been disclosed such as that by Kitware, Inc.

The heart is an internal organ that repeatedly contracts and expands. Upon contraction, the ventricular apex at the distal aspect of the ventricles moves toward both the aortic valve and the mitral value. Further, the entire myocardium contracts in a twisting manner. Conventional technologies are not specialized for movements of the heart and therefore, tracing the characteristic movements of the heart is difficult; and the same is true for other internal organs besides the heart, such as the lungs, the liver, and the kidneys.

SUMMARY

According to an aspect of an embodiment, a computer-readable recording medium stores a display program for displaying simulation results and causing a computer to execute a process that includes detecting from a first element group included in a simulation model and having physical values according to position in the simulation model of a first unit time, a first element string of elements along a first line that passes through the simulation model; extracting from the first element string, first physical values of the elements of the first element string; setting a second line that passes through the simulation model of a second unit time that is subsequent to the first unit time; detecting from a second element group included in the simulation model and having physical values according to position in the simulation model of the second unit time, a second element string that is along the second line and corresponds to the first element string; extracting from the second element string, second physical values of elements of the second element string; and displaying the first physical values and the second physical values.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 3 is a diagram depicting an example of the contents of a database (DB);

FIG. 6 is a diagram depicting an example of the data structures of tetra element strings for each time ti;

FIG. 7 is a diagram depicting an example of the data structures of inter-element distances for each time ti;

FIG. 8 is a flowchart of an example of a display process performed by a display apparatus 500 according to the first embodiment;

FIG. 10 is a diagram depicting an example of the data structures of the tetra element strings for each time ti;

FIG. 11 is a diagram depicting an example of the data structures of the inter-element distance for each time ti;

FIG. 14 is a diagram depicting an example of the data structures of the tetra element strings for each time ti;

FIG. 15 is a diagram depicting an example of the data structures of the inter-element distance for each time ti; and FIG. 16 is a flowchart of an example of the display process performed by the display apparatus 500 according to the third embodiment.

DESCRIPTION OF EMBODIMENTS

Preferred embodiments of the present invention will be explained with reference to the accompanying drawings. Physical values of internal organs, such as the heart, in humans and animals vary with time. To express such internal organs, in the present embodiment, a 3-dimensional model of an internal organ is adopted as a simulation model. The 3-dimension model of an internal organ is a set of tetrahedral elements (unstructured grid data) called tetra elements. Each tetra element has a physical value corresponding to the position of the tetra element. A physical value is a value indicative of the behavior of the cardiac muscle corresponding to the tetra element; and, for example, pressure [KPa], work [J/ml], workrate [J/s·ml] are adopted as physical values.

In the present embodiment, to trace in time series, the behavior of an internal organ such as the heart, the display apparatus specifies a line that is to be traced in the 3-dimensional model of the internal organ, extracts a string of physical values from a string of tetra elements corresponding to the specified line, and displays the string of physical values for each unit of time. Thus, the display apparatus can trace the behavior along a line specified for tracing.

In the present embodiments, although description is given using a 3-dimensional model of a heart as one example of an internal organ, implementation may be by a 3-dimensional model of another internal organ other than the heart. Hereinafter, the 3-dimensional model of the heart will be referred to as a “heart model”. Although a heart models exists for each unit of time, the heart, which is the basis of the model, is the heart of one individual.

Figure 1A:
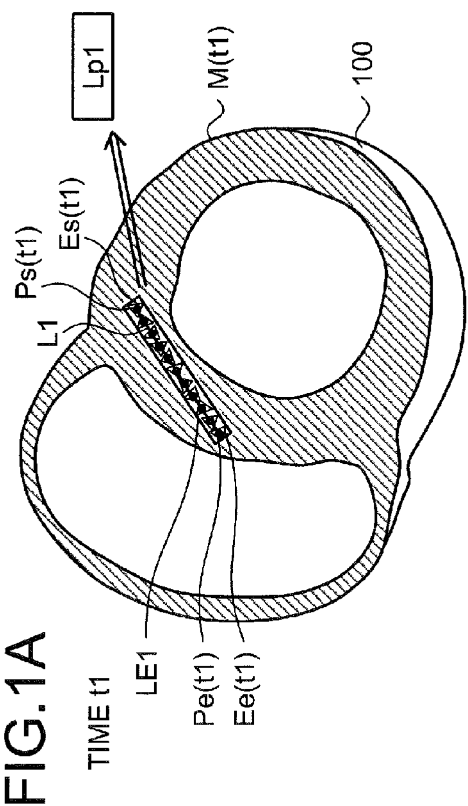
FIGS. 1A, 1B, and 1C are diagrams depicting a behavior tracing example for the heart model according to a first embodiment.
Figure 1B:
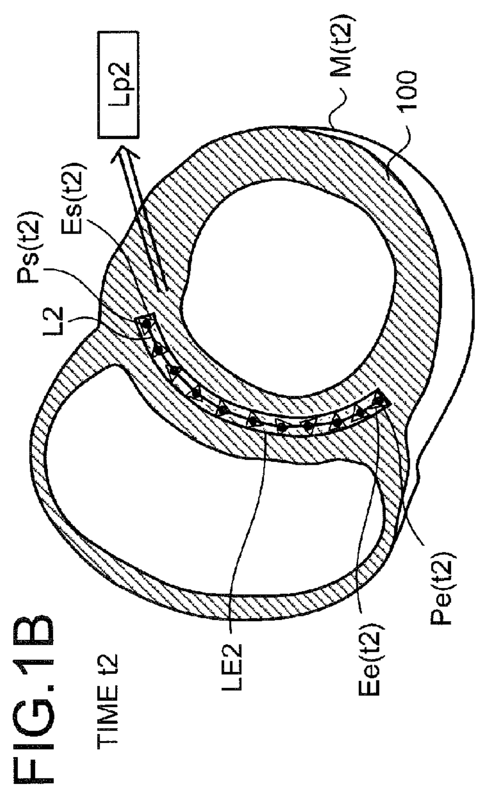
Figure 1C:
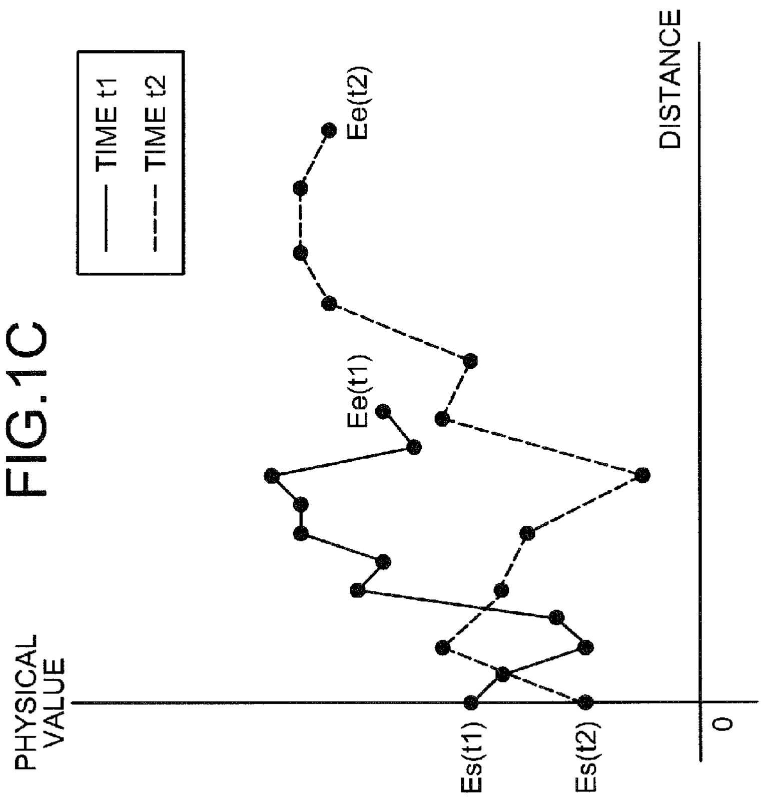

FIGS. 1A, 1B, and 1C are diagrams depicting a behavior tracing example for the heart model according to a first embodiment. In FIGS. 1A, 1B, and 1C, heart models at time t1 and at time t2 subsequent to time t1 are used to describe the behavior tracing example for the heart model.

In FIGS. 1A and 1B, a heart model M(t1) at time t1 and a heart model M(t2) at time t2 are depicted. A heart model at a time ti (1≤i≤n) is indicated as a heart model M(ti). The display apparatus, consequent to an input operation via an input device such as a mouse, specifies as a line, cardiac muscle that is to be traced in the heart model M(t1) at time t1. The line is not limited to a straight line and may be a part of a curve.

Although in FIGS. 1A and 1B, the heart model M(ti) is depicted as a cross section of the heart model M(ti), this type display processing is commonly known and therefore, description thereof is omitted. Further, the display apparatus specifies a line on a cross section 100 of the heart model M(ti), whereby the interior of the heart and cardiac muscle of an interior surface can be specified. If the heart model is not cross-sected, the display apparatus can specify cardiac muscle at the external surface of the heart.

If a line has been specified, a tetra element that includes the starting end (start point Ps) of the line is identified. Similarly, a tetra element that includes the terminal end (end point Pe) of the specified line is identified. A tetra element that includes the start point Ps is regarded as a tetra element Es and a tetra element that includes the end point Pe is regarded as a tetra element Ee.

A line specified in a heart model at time ti (1≤i≤n) is regarded as a line Li; the start point of the line Li is regarded as a start point Ps(ti); a tetra element that includes the start point Ps(ti) is regarded as a tetra element Es(ti); the end point of the line Li is regarded as an end point Pe(ti); and a tetra element that includes the end point Pe(ti) is regarded as a tetra element Ee(ti). Accordingly, in the case of time t1, a line L1, a start point Ps(t1), a tetra element Es(t1), an end point Pe(t1), and a tetra element Ee(t1) are designated.

Further, by specifying the line L1, a tetra element string LE1 through which the line L1 passes and that includes the start point Ps(t1) and the end point Pe(t1) is extracted. In the first embodiment, a point that divides the line L1 at equal intervals is regarded as a division point. In FIGS. 1A and 1B, black circles on the line Li represents the start point, division points, and the end point. Triangles encompassing a black circle represent tetra elements. A string of tetra elements that includes a start point, 1 or more division points, and an end point is referred to as a tetra element string LEi. Each tetra element making up the tetra element string LEi has a unique physical value and therefore, a physical value string Lpi is extracted from the tetra element string LEi. In the case of time t1, a physical value string Lp1 is extracted from the tetra element string LE1. Thus, the physical value string Lp1 can be obtained for the line L1 at time t1, corresponding to cardiac muscle.

When the time changes from time t1 to time t2, the position of a tetra element group varies consequent to movements of the heart. Therefore, the tetra element Es(t1) including the start point Ps(t1) and the tetra element Ee(t1) including the end point Pe(t1) at time t1, become tetra elements Es(t2) and Ee(t2) in the heart model at time t2. A start point Ps(t2) included in the tetra element Es(t2) is the center of gravity of the tetra element Es(t2). An end point Pe(t2) included in the tetra element Ee(t2) is the center of gravity of the tetra element Ee(t2). A line L2 is formed by connecting the start point Ps(t2) and the end point Pe(t2).

Similarly for time t2, a point that divides the line L2 at equal intervals is regarded as a division point, and a tetra element string LE2 is obtained that includes the start point Ps(t2) and the end point Pe(t2) of the line L2 as well as 1 or more division points between the start point Ps(t2) and the end point Pe(t2). Each tetra element making up the tetra element string LE2 also has a unique physical value and therefore, a physical value string Lp2 is extracted from the tetra element string LE2. Thus, a physical value string Lp2 can be obtained for the line L2 at time t2, corresponding to cardiac muscle. The physical value string Lp1 obtained from the line L1 at time t1 and the physical value string Lp2 obtained from the line L2 at time t2 are graphed and displayed.

FIG. 1C depicts an example of a graphed display of the physical value string Lp1 obtained from the line L1 at time t1 and the physical value string Lp2 obtained from the line L2 at time t2. The horizontal axis represents a relative distance between the detected tetra element strings. The vertical axis represents the magnitude of the physical value. With respect to distance plotted along the horizontal axis, the tetra elements Es(t1), Es(t2) that respectively include the start points at the times t1 and t2 are plotted at the origin, i.e., at “0”.

Thus, by graphing and displaying the physical value strings Lp1 and Lp2, which have identical tetra elements at respective ends and are expressed in time series, the manner in which the physical values of the cardiac muscle specified as a line, vary consequent to movement of the heart can be understood. In FIG. 1C, although the physical value string Lp1 at time t1 and the physical value string Lp2 at time t2 are displayed on the same graph, the physical value strings Lp1 and Lp2 may be displayed on independent graphs. Further, in FIGS. 1A, 1B, and 1C, although description is given with respect to time t1 and time t2, physical value strings Lp3, Lp4, . . . , Lpn at times t3, t4, . . . , to subsequent to time t2 may be similarly displayed.

Figure 2:
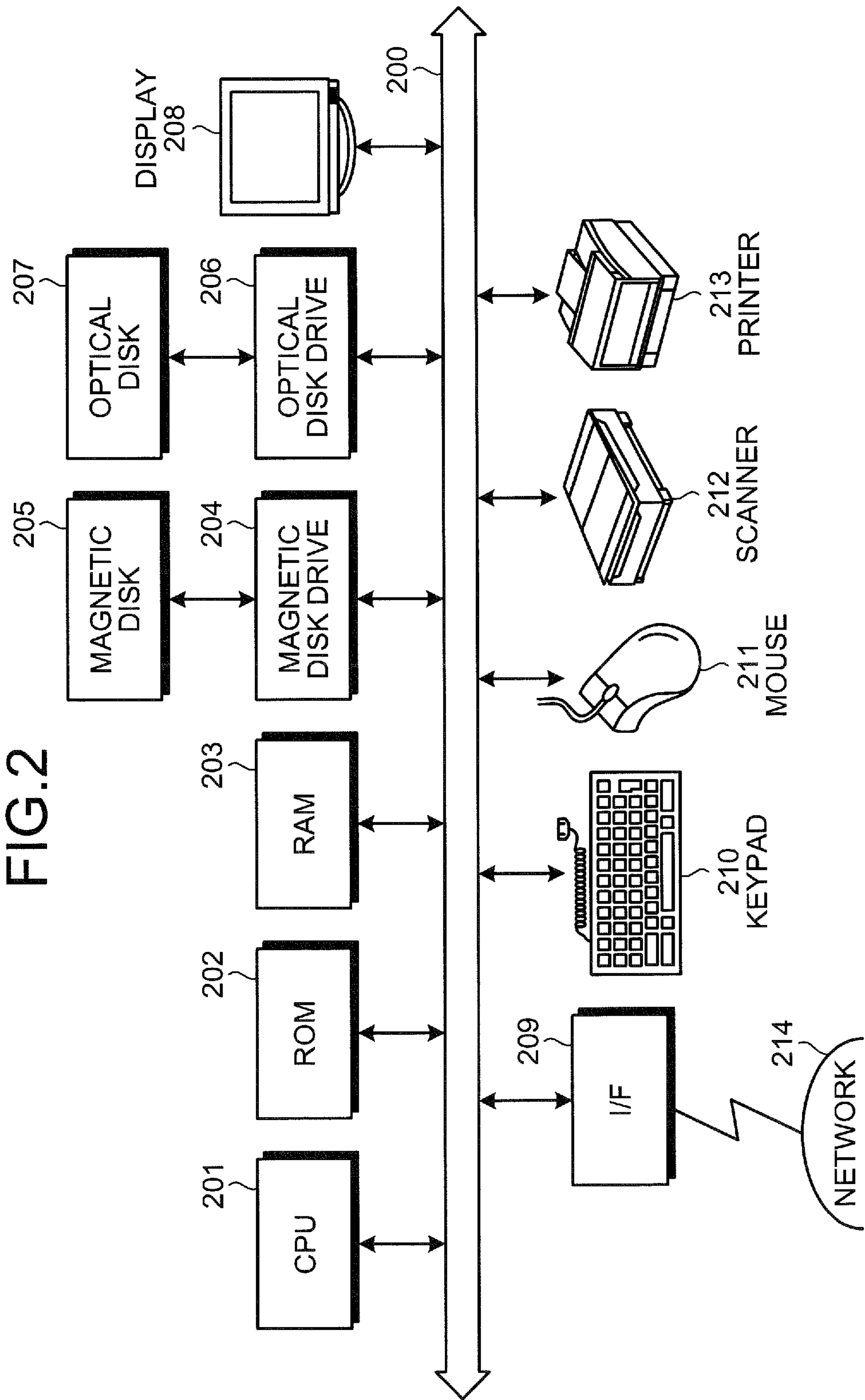
FIG. 2 is a block diagram of a hardware configuration of the display apparatus according to the embodiments.

FIG. 2 is a block diagram of a hardware configuration of the display apparatus according to the embodiments. As depicted in FIG. 2, the display apparatus includes a central processing unit (CPU) 201, read-only memory (ROM) 202, random access memory (RAM) 203, a magnetic disk drive 204, a magnetic disk 205, an optical disk drive 206, an optical disk 207, a display 208, an interface (I/F) 209, a keypad 210, a mouse 211, a scanner 212, and a printer 213, respectively connected by a bus 200.

The CPU 201 governs overall control of the display apparatus. The ROM 202 stores various types of programs such as a boot program. The RAM 203 is used as a work area of the CPU 201. The magnetic disk drive 204, under the control of the CPU 201, controls the reading and writing of data with respect to the magnetic disk 205. The magnetic disk 205 stores data written thereto under the control of the magnetic disk drive 204.

The optical disk drive 206, under the control of the CPU 201, controls the reading and writing of data with respect to the optical disk 207. The optical disk 207 stores data written thereto under the control of the optical disk drive 206, the data being read out from the optical disk 207 by a computer.

The display 208 displays, for example, data such as text, images, functional information, etc., in addition to a cursor, icons, and/or tool boxes. A liquid crystal display, a plasma display, etc., may be employed as the display 508.

The I/F 209 is connected to a network 214 such as a local area network (LAN), a wide area network (WAN), and the Internet through a communication line and is connected to other apparatuses through the network 214. The I/F 209 administers an internal interface with the network 214 and controls the input/output of data from/to external apparatuses. For example, a modem or a LAN adaptor may be employed as the I/F 209.

The keypad 210 includes, for example, keys for inputting letters, numerals, and various instructions and performs the input of data. Alternatively, a touch-panel-type input pad or numeric keypad, etc. may be adopted. The mouse 211 is used to move the cursor, select a region, or move and change the size of windows. A track ball or a joy stick may be adopted provided each respectively has a function similar to a pointing device.

The scanner 212 optically reads an image into the display apparatus. The scanner 212 may have an optical character reader (OCR) function. The printer 213 prints image data and text data. The printer 213 may be, for example, a laser printer, an inkjet printer, and the like. Further, configuration may be such that at least any one among the optical disk drive 206, the optical disk 207, the display 208, the keypad 210, the mouse 211, the scanner 212, and the printer 213 is omitted.

FIG. 3 is a diagram depicting an example of the contents of a database (DB). In FIG. 3, a DB stores data structures D1 to Dn for each group of tetra elements at the times t1 to tn. In other words, from the data structure for the group of tetra elements at a time ti, a heart model for time ti is generated. Here, a data structure Di for a tetra element group at time ti is a data structure having for each tetra element, values of an ID field, a first vertex field to a fourth vertex field, a center of gravity field, and a physical value field.

The ID field stores a tetra element ID: i ($1 \leq j \leq m$). A tetra element ID is identifier information uniquely identifying a tetra element. A tetra element of the tetra element ID "j" is a tetra element Ej(ti). The first vertex field to fourth vertex field respectively store coordinate values of a first vertex v1(Ej(ti)) to a fourth vertex v4(Ej(ti)) for the tetra element Ej(ti). For the sake of convenience, coordinate values will be indicated as v1(Ej(ti)) to v4(Ej(ti)). The first vertex v1(Ej(ti)) to the fourth vertex v4(Ej(ti)) are respectively the vertices of the tetra element Ej(ti), which is a tetrahedron.

The center of gravity field stores center of gravity coordinate values for the center of gravity g(Ej(ti)) of the tetra element Ej(ti). For the sake of convenience, the coordinate values will be indicated as g(Ej(ti)). The physical value field stores a physical value p(Ej(ti)) assigned to the center of gravity g(Ej(ti)) of the tetra element Ej(ti). As described, the physical value p(Ej(ti)) is a value indicative of the behavior of the cardiac muscle corresponding to the tetra element; and, for example, pressure [KPa], work [J/ml], workrate [J/s·ml] are adopted as physical values.

Figure 4:
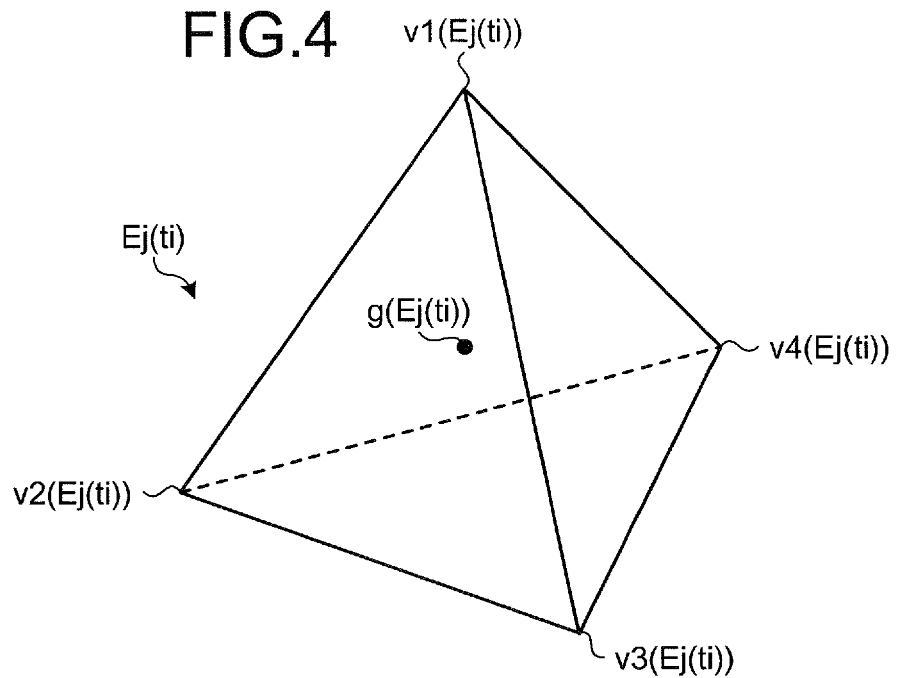
FIG. 4 is a diagram depicting a tetra element Ej(ti) of a data structure Di.

FIG. 4 is a diagram depicting the tetra element Ej(ti) of the data structure Di. The shape of the tetra element Ej(ti) is a tetrahedron having the first vertex v1(Ej(ti)) to the fourth vertex v4(Ej(ti)). Further, the physical value p(Ej(ti)) is assigned to the center of gravity g(Ej(ti)).

Figure 5:
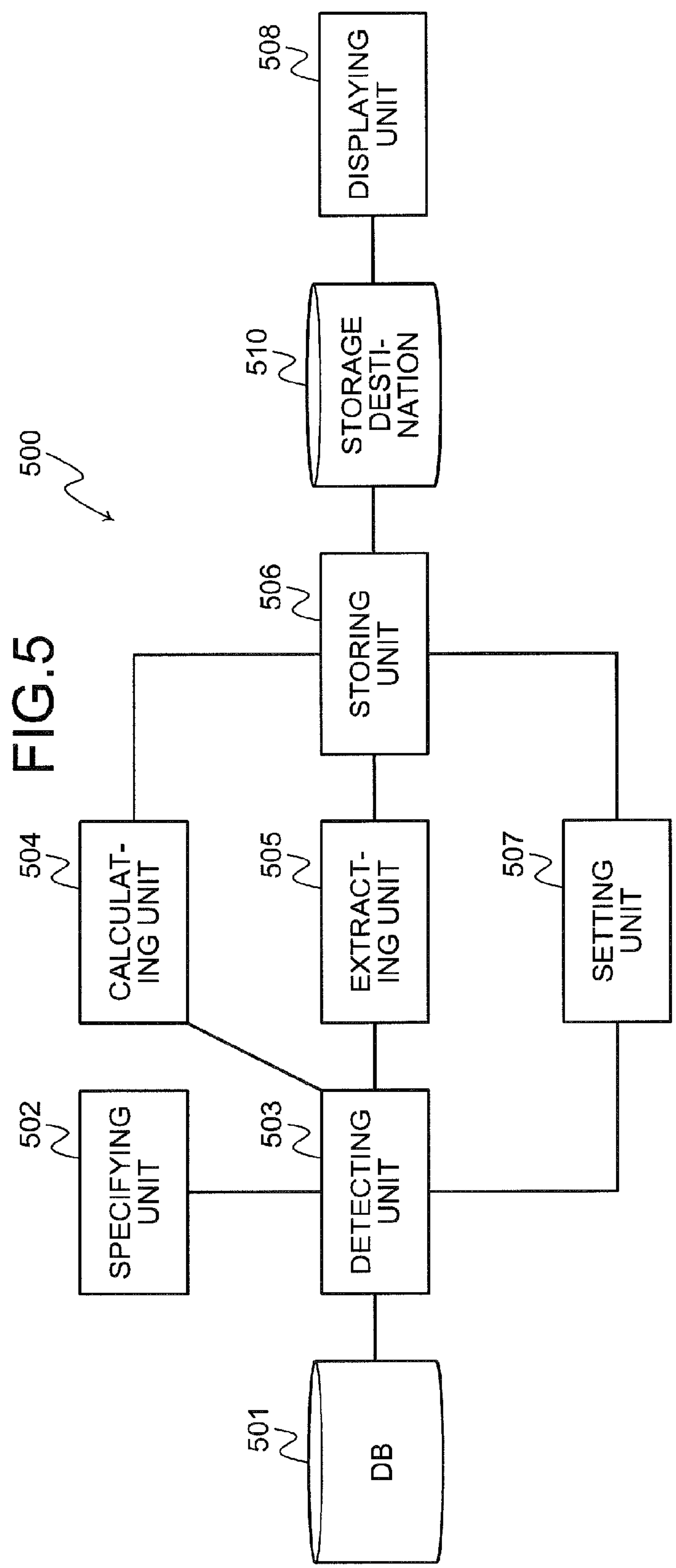
FIG. 5 is a block diagram of a functional configuration of the display apparatus.

FIG. 5 is a block diagram of a functional configuration of the display apparatus. A display apparatus 500 has a DB 501 and a storage destination 510. The DB 501 stores the data structures D1 to Dn depicted in FIG. 3. The storage destination 510 stores data from a storing unit 506. Functions of the DB 501 and the storage destination 510 are implemented by a storage device such as the ROM 202, the RAM 203, the magnetic disk 205, and the optical disk depicted in FIG. 2.

The display apparatus 500 includes a specifying unit 502, a detecting unit 503, a calculating unit 504, an extracting unit 505, the storing unit 506, a setting unit 507, and a displaying unit 508. Functions of the specifying unit 502, the detecting unit 503, the calculating unit 504, the extracting unit 505, the storing unit 506, the setting unit 507, and the displaying unit 508 are implemented by, for example, executing on the CPU 201, a program stored in a storage device such as the ROM 202, the RAM 203, the magnetic disk 205, and the optical disk depicted in FIG. 2, or by the I/F 209.

The specifying unit 502 receives specification of various types of information via an input device such as the keypad 210 and the mouse 211. For example, the specifying unit 502 receives a time step count i. For example, if a time step count of i=n is specified, the display apparatus 500 reads from the DB 501, the data structure D1 for time t1 to the data structure Dn for time tn. Further, the specifying unit 502 receives specification of a line. For example, as depicted in FIG. 1A, the specifying unit 502 receives specification of a line in a cross section or on an exterior surface of the heart model M(t1). The specified line corresponds to cardiac muscle that is to be traced. Thus, movement of the heart at a position to be checked by the user can be traced locally by specification of a line by a user operation.

The detecting unit 503 detects from a first element group that is included in the simulation model and has physical values according to position in the simulation model of a first unit time, a first element string that is a plurality of elements along a first line passing through the simulation model. For example, the detecting unit 503 detects from the first element group of the first unit time and having physical values according to position in the internal organ model of the first unit time, a first element string that includes the first line, which passes through the internal organ model of the first unit time. The first element group is a data structure having physical values according to position in the internal organ model of the first unit time. For example, if the first unit time is time t1, the internal organ model at the first unit time is the heart model at time t1; and the first element group is the data structure D1 of the tetra element group at time t1. Further, if the first unit time is time t1, the first line is the line L1 as depicted in FIG. 1A; and the first element string is the tetra element string LE1 that includes the line L1.

The detecting unit 503 evenly divides the line by a given number. A point on the divided line is referred to as a division point. The detecting unit 503 detects a tetra element that includes a division point. In this case, tetra elements that include the start point and the end point at the terminal ends of the line and 1 or more division points is a tetra element string. Thus, by evenly dividing the line by a given number, the number of elements (element count) in a tetra element string can be controlled to a given number and the number of physical values (extraction count) extracted by the extracting unit 505 described hereinafter can be controlled to a given number. Thus, the speed of calculation can be increased.

The calculating unit 504 calculates an inter-element distance for each element in the first element string. For example, the calculating unit 504 calculates the distance between the centers of gravity of an element adjacent to a given element in the first element string and of the given element in the first element string. The calculation function of the calculating unit 504 is selectively executed. For example, in the display of a graph, if the inter-element distance between adjacent tetra elements is to be expressed, the calculating unit 504 calculates the inter-element distance. As a result, at the displaying unit 508, a graph is displayed according to the inter-element distance. On the other hand, in the case of simplification, the calculating unit 504 is not executed. In this case, the displaying unit 508 simply plots the physical value at equal intervals along the distance axis.

The extracting unit 505 extracts from the first element string, first physical values of the elements of the detected first element string. For example, the extracting unit 505 extracts from the first element string, a first physical value string of physical values of the elements of the first element string detected by the detecting unit 503. For example, if the first unit time is time t1, the first physical value string of the first element string is a set of physical values assigned to the tetra elements in a tetra element string. When a tetra element in the first tetra element string is a tetra element Ej(t1), the physical value thereof is a physical value p(Ej(t1)) as depicted in FIG. 3.

The storing unit 506 correlates and stores to a storage device, the first element string and the first physical value string extracted by the extracting unit 505. For example, the storing unit 506 correlates and stores to the storage destination 510, the first element string and the first physical value string. If the first unit time is time t1, the storing unit 506 correlates and stores to the storage destination 510, the tetra element string LE1 and the physical value string Lp1 thereof.

The setting unit 507 sets a second line that passes through the simulation model of a second unit time subsequent to the first unit time. For example, the setting unit 507 sets in an internal organ model of a second unit time, the second line that is related to the first line and passes through the internal model of each second unit time subsequent to the first unit time. If the first unit time is time t1 and the second unit time is time t2, as depicted in FIG. 1B, the setting unit 507 sets the line L2 in the internal organ model M(t2).

For example, the setting unit 507 identifies from a second element group of the second unit time, the starting-end element of the second unit time and the terminal-end element of the second unit time, respectively elements identical to a starting-end element of the first unit time (i.e., the starting end of the first line) and a terminal-end element of the first unit time (i.e., the terminal end of the first line). For example, if the second unit time is time t2, the second element group of the second unit time is the data structure D2 of the heart model M(t2).

Further, for example, if the first unit time is time t1, the starting-end element of the first unit time (i.e., the starting end of the first line) is the tetra element Es(t1), which is the start point Ps(t1) of the line L1. Further, for example, if the first unit time is time t1, the terminal-end element of the first unit time (i.e., the terminal end of the first line) is the tetra element Ee(t1), which is the end point Pe(t1) of the line L1.

Further, for example, if the second unit time is time t2, the starting-end element of the second unit time (i.e., an element identical to the starting-end element of the first unit time) is the tetra element Es(t2), which is the start point Ps(t2). Further, for example, if the second unit time is time t2, the terminal-end element of the second unit time (i.e., an element identical to the terminal-end element of the first unit time) is the tetra element Ee(t2), which is the end point Pe(t2).

The setting unit 507 sets the second line connecting the identified starting-end element of the second unit time and the identified terminal-end element of the second unit time. For example, the setting unit 507 sets the line L2, which connects the tetra element Es(t2) and the tetra element Ee(t2). Further, for example, the setting unit 507 sets as the second line, a line connecting the center of gravity g(Es(t2)) of the tetra element Es(t2) and the center of gravity g(Ee(t2)) of the tetra element Ee(t2).

The setting unit 507, for example, connects the starting-end element of the second unit time and the terminal-end element of the second unit time by a straight line to set the second line. However, when the straight line is projected on a face, if at least a portion of the projected line is not present on the face, the setting unit 507 executes a correction process. For example, in the cross section of the heart model M(t2) in FIG. 1B, connection of the start point Ps(t2) and the end point Pe(t2) by a straight line results in passage through a space with no tetra elements. In such a case, the setting unit 507 sets the line to be within a given distance from a border of the cross section. As a result, the setting unit 507, as depicted in the heart model M(t2) in FIG. 1B, can set the line L2 on a cross section. Further, with respect to the second line, the detecting unit 503, the calculating unit 504, the extracting unit 505, and the storing unit 506 execute processes identical to those for the first line.

The displaying unit 508 displays the extracted first physical values and second physical values. For example, the displaying unit 508 displays the first element string and the first physical value string stored by the first storing unit 506 and displays a second element string and the second physical value string stored by the second storing unit 506. Here, description will be given using as an example, the first element string and the first physical value string stored by the first storing unit 506.

The displaying unit 508 displays the tetra element string LE1 and the physical value string Lp1. For example, as depicted in FIG. 1C, the displaying unit 508 expresses each tetra element of the tetra element string LE1 as a point on a curve in a graph, plotting physical values against the vertical axis, using the horizontal axis direction as the arrangement direction of the tetra element string LE1. If inter-element distances are calculated by the calculating unit 504, the displaying unit 508 plots against the horizontal axis according to the inter-element distance. Display is similarly performed with respect to the second element string and the second physical value string stored by the second storing unit 506.

An example of the contents stored to the storage destination 510 by the storing unit 506 will be described. The storage destination 510 stores the tetra element string and inter-element distances for each time ti. Description will be given with reference to FIGS. 6 and 7.

FIG. 6 is a diagram depicting an example of the data structures of the tetra element strings for each time ti. The storage destination 510 stores the data structures of tetra element strings of the time step count n specified by the specifying unit 502. In FIG. 6, the tetra elements E1(t1) to E1(tn) are the tetra elements Es(t1) to Es(tn) that include the start points at the times t1 to tn and the tetra elements E50(t1) to E50(tn) are the tetra elements Ee(t1) to Ee(tn) that include the end points at the times t1 to tn.

Further, the tetra element name is a pointer to the data structure Di and therefore, storage of the tetra element name enables the display apparatus 500 to extract from the data structure, the physical value of the tetra element specified by the tetra element name. For example, for the tetra element E1(t1), specification of the tetra element name "E1(t1)" enables the display apparatus 500 to identify from the data structure D1, the physical value p(E1(t1)) of the tetra element E1(t1).

FIG. 7 is a diagram depicting an example of the data structures of the inter-element distances for each time ti. The storage destination 510 stores the data structures of inter-element distances of the time step count n specified by the specifying unit 502.

FIG. 8 is a flowchart of an example of a display process performed by the display apparatus 500 according to the first embodiment. The display apparatus 500, via the specifying unit 502, specifies the time step count n, and sets an index i of time ti to be i=1 (step S801). The display apparatus 500 specifies a line Li in a heart model M(ti) of time ti (step S802). The display apparatus 500, via the detecting unit 503, detects from the line Li, a start point Es(ti) and an end point Ee(ti), and stores the element IDs (step S803). In FIG. 6, when i=1, the element ID of the start point Es(t1) is "E1" and the element ID of the end point Ee(t1) is "E50".

The display apparatus 500, via the detecting unit 503, evenly divides the line Li and determines division points (step S804). The display apparatus 500, via the detecting unit 503, detects a tetra element string LEi that includes the start point, the end point, and the division points (step S805). The display apparatus 500, via the calculating unit 504, calculates inter-element distances (step S806).

The display apparatus 500, via the extracting unit 505, extracts from the tetra element string LEi, a physical value string Lpi (step S807). The display apparatus 500, via the storing unit 506, correlates and stores the physical value string Lpi and the tetra element string LEi (step S808). The display apparatus 500, via the storing unit 506 and for the inter-element distances of the tetra element string LEi as well, correlates and stores the tetra element string LEi and the physical value string Lpi.

The display apparatus 500 increments the index i (step S809). The display apparatus 500 determines whether i>n is true (step S810). If i>n is not true (step S810: NO), the display apparatus 500, via the setting unit 507, sets a line Li in the heart model M(ti) of time ti (step S811), and returns to step S803. Thus, at each time ti, steps S803 to S811 are executed. At step S810, if i>n is true (step S810: YES), the display apparatus 500, via the displaying unit 508, performs graphing and display (step S812), whereby as depicted in FIG. 1C, a graph is displayed and a series of the operations according to the flowchart is ended.

Thus, in the first embodiment, tetra elements of both ends of a line are respectively the same elements at each time ti, whereby at each time ti, the tetra elements of both ends are fixed. Therefore, the varying movement of cardiac muscle over time and corresponding to the user-specified line can be traced.

Further, at each time ti, the line is evenly divided, whereby the element count of the tetra element string at each time ti can be set to be identical. Therefore, the number of tetra elements to be traced is controlled, enabling faster display processing.

A second embodiment will be described. In the first embodiment, an example is described where the tetra elements at both ends of the tetra element string LEi specified by the line Li (or set), respectively are fixed to not change even at different times ti, and the varying movement of cardiac muscle over time and corresponding to the line L1 specified by the user is traced in time series. In contrast, in the second embodiment, an example will be described where the line Li is fixed even at different times ti, and the movement of cardiac muscle corresponding to the line Li is traced by the tetra element string LEi passing through the line Li at each time ti.

In other words, in a 3-dimensional space in which the heart model M(ti) is arranged, although the heart model M(ti) moves at each time ti, the line exists at the same position irrespective of the time ti. Therefore, the movement of the cardiac muscle that over time, moves into the position of the user-specified line can be traced. The display apparatus 500 of the second embodiment differs from that of the first embodiment in terms of the setting unit 507 alone and therefore, the setting unit 507 alone will be described and components other than the setting unit 507 are given the same reference numerals used in the first embodiments and corresponding description thereof will be omitted.

Figure 9C:
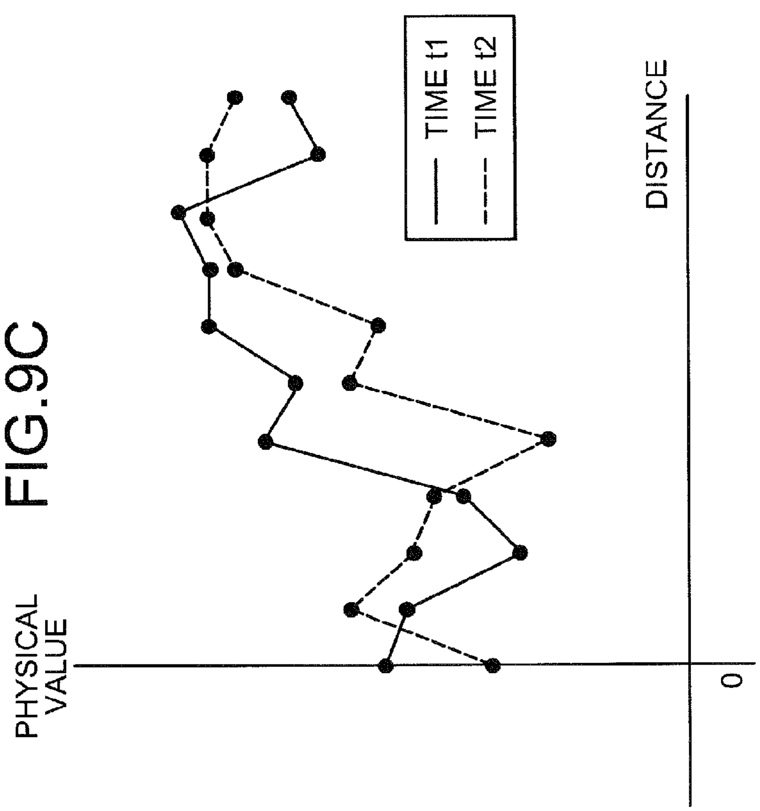
FIGS. 9A, 9B, and 9C are diagrams depicting a behavior tracing example of a heart model according to a second embodiment.
Figure 9A:
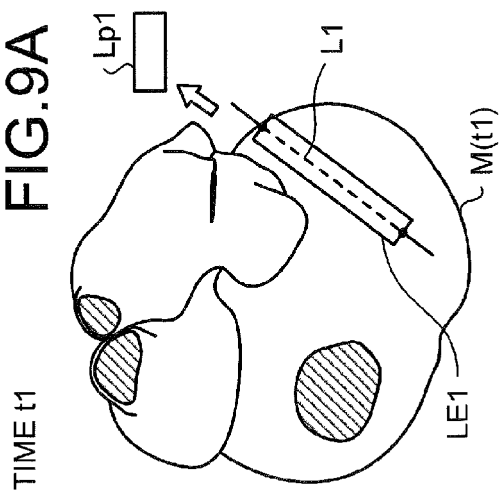
Figure 9B:
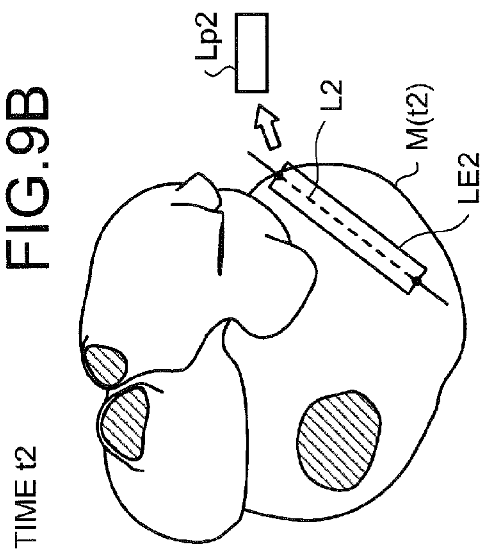

FIGS. 9A, 9B, and 9C are diagrams depicting a behavior tracing example of the heart model according to the second embodiment. Unlike in the first embodiment, the line L1 in the heart model M(t1) of time t1 and the line L2 in the heart model M(t2) of time t2 are at the same position in a 3-dimensional coordinate system at times t1 and t2.

In FIGS. 9A and 9B, the display apparatus 500, via the detecting unit 503, detects a tetra element string LE1 that includes the line L1, and via the extracting unit 505, extracts a physical value string Lp1 of the tetra element string LE1. When the time changes from time t1 to time t2, the display apparatus 500, via the setting unit 507, acquires position information of the line L1 and sets in the heart model M(t2) of time t2, the line L2 to be at the same position as the line L1. The display apparatus 500, via the detecting unit 503, detects a tetra element string LE2 that includes the line L2, and via the extracting unit 505, extracts a physical value string Lp2 of the tetra element string LE2.

In FIG. 9C, the display apparatus 500, via the displaying unit 508, graphs and displays the extracted physical value string Lpi. Thus, in the second embodiment, the line Li is fixed even when the time ti changes and the movement of cardiac muscle corresponding to the line Li can be traced by each tetra element string LEi that passes through the line Li at each time ti.

An example of the contents stored to the storage destination 510 by the storing unit 506 will be described. The storage destination 510 stores a tetra element string LEi and inter-element distances for each time ti. Description will be given with reference to FIGS. 10 and 11.

FIG. 10 is a diagram depicting an example of the data structures of the tetra element strings for each time ti. The storage destination 510 stores the data structures of tetra element strings of the time step count n specified by the specifying unit 50. The tetra element name is a pointer to the data structure. Therefore, storage of the tetra element name enables the display apparatus 500 to extract from the data structure, the physical value of the tetra element specified by the tetra element name. For example, for the tetra element E1(t1), specification of the tetra element name "E1(t1)" enables the display apparatus 500 to identify from the data structure D1, the physical value p(E1(t1)) of the tetra element E1(t1). Unlike the first embodiment, in the second embodiment, at each time ti, the tetra elements at both ends of the line are not fixed.

FIG. 11 is a diagram depicting an example of the data structures of the inter-element distance for each time ti. The storage destination 510 stores the data structures of inter-element distances of the time step count n specified by the specifying unit 502.

Figure 12:
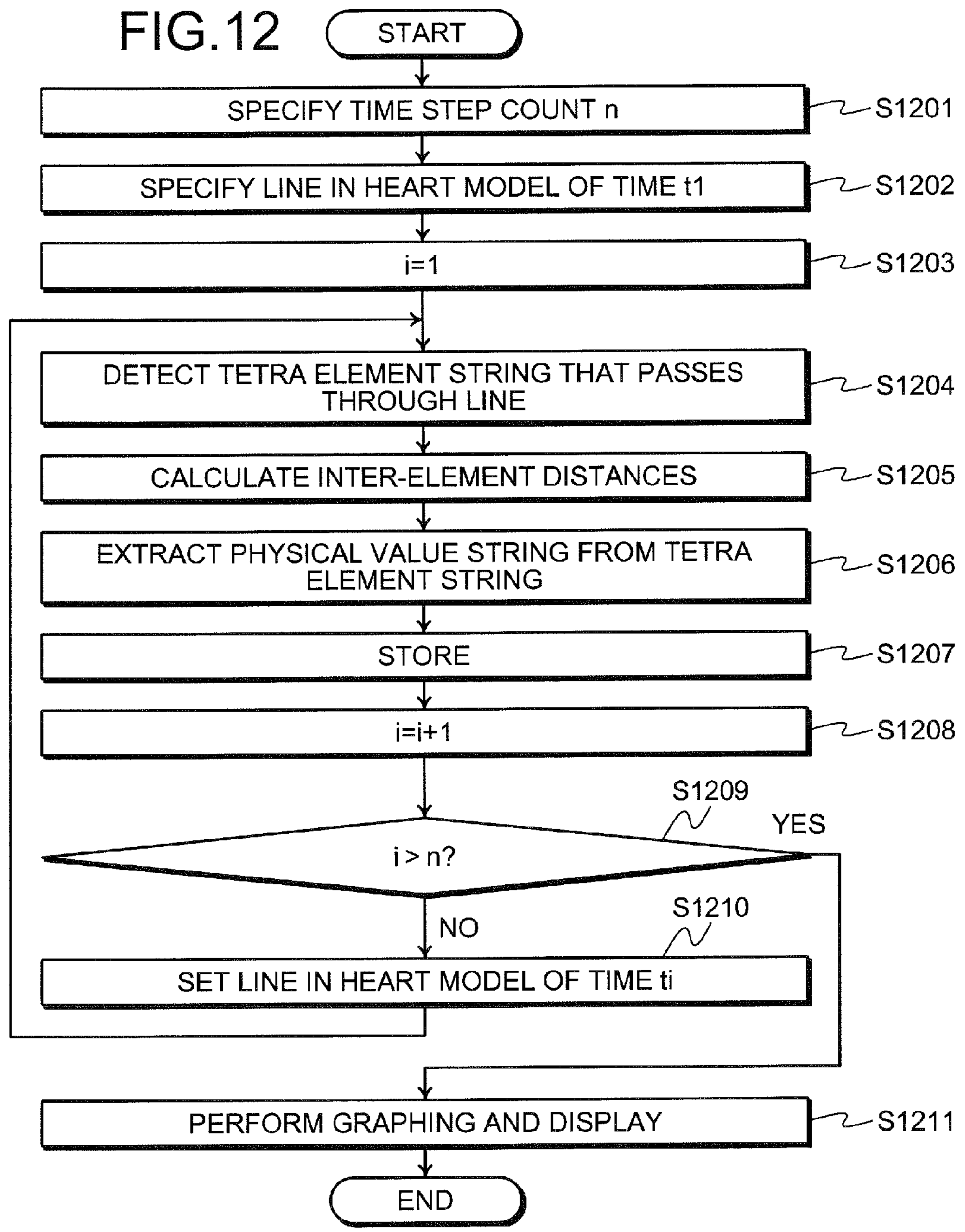
FIG. 12 is a flowchart of an example of the display process performed by the display apparatus 500 according to the second embodiment.

FIG. 12 is a flowchart of an example of the display process performed by the display apparatus 500 according to the second embodiment. The display apparatus 500, via the specifying unit 502, specifies the time step count n (step S1201), and specifies the line L1 in the heart model M(t1) of time t1 (step S1202). The display apparatus 500 sets the index i of time ti to be i=1 (step S1203).

The display apparatus 500, via the detecting unit 503, detects a tetra element string that passes through the line Li in the heart model M(ti) (step S1204). The display apparatus 500, via the calculating unit 504, calculates inter-element distances (step S1205).

The display apparatus 500, via the extracting unit 505, extracts from the tetra element string LEi, a physical value string Lpi (step S1206). The display apparatus 500, via the storing unit 506, correlates and stores the physical value string Lpi and tetra element string LEi (step S1207). The display apparatus 500, via the storing unit 506 and for the inter-element distances of the tetra element string LEi as well, correlates and stores the tetra element string LEi and the physical value string Lpi.

The display apparatus 500 increments the index i (step S1208). The display apparatus 500 determines whether i>n is true (step S1209). If i>n is not true (step S1209: NO), the display apparatus 500, via the setting unit 507, sets the line Li in the heart model M(ti) of time ti (step S1210), and returns to step S1204. Thus, at each time ti, steps S1204 to S1210 are executed. At step S1209, if i>n is true (step S1209: YES), the display apparatus 500, via the displaying unit 508, performs graphing and display (step S1211), whereby as depicted in FIG. 9C, a graph is displayed and a series of the operations according to the flowchart is ended.

Thus, in the second embodiment, the line Li is fixed irrespective of the time ti and the movement of cardiac muscle corresponding to the line Li is traced by each tetra element string LEi that passes through the line Li at each time ti. In other words, in a 3-dimensional space in which the heart model M(ti) is arranged, although the heart model M(ti) moves at each time ti, the line Li is present at the same position in the 3-dimensional space irrespective of the time ti. Therefore, the movement of cardiac muscle that over time, moves into the position of the user-specified line Li can be traced.

A third embodiment will be described. In the first and second embodiments, the line L1 is specified, and the movement over time of cardiac muscle corresponding to the line Li and the movement over time of cardiac muscle into the position of the line Li are traced. In contrast, in the third embodiment, the movement of cardiac muscle corresponding to tetra elements of a tetra element string that passes through a first specified line is traced, whereby the types of physical values of the tetra elements and the extent of movement of the tetra elements over time can be understood.

Figures 13A, 13B:
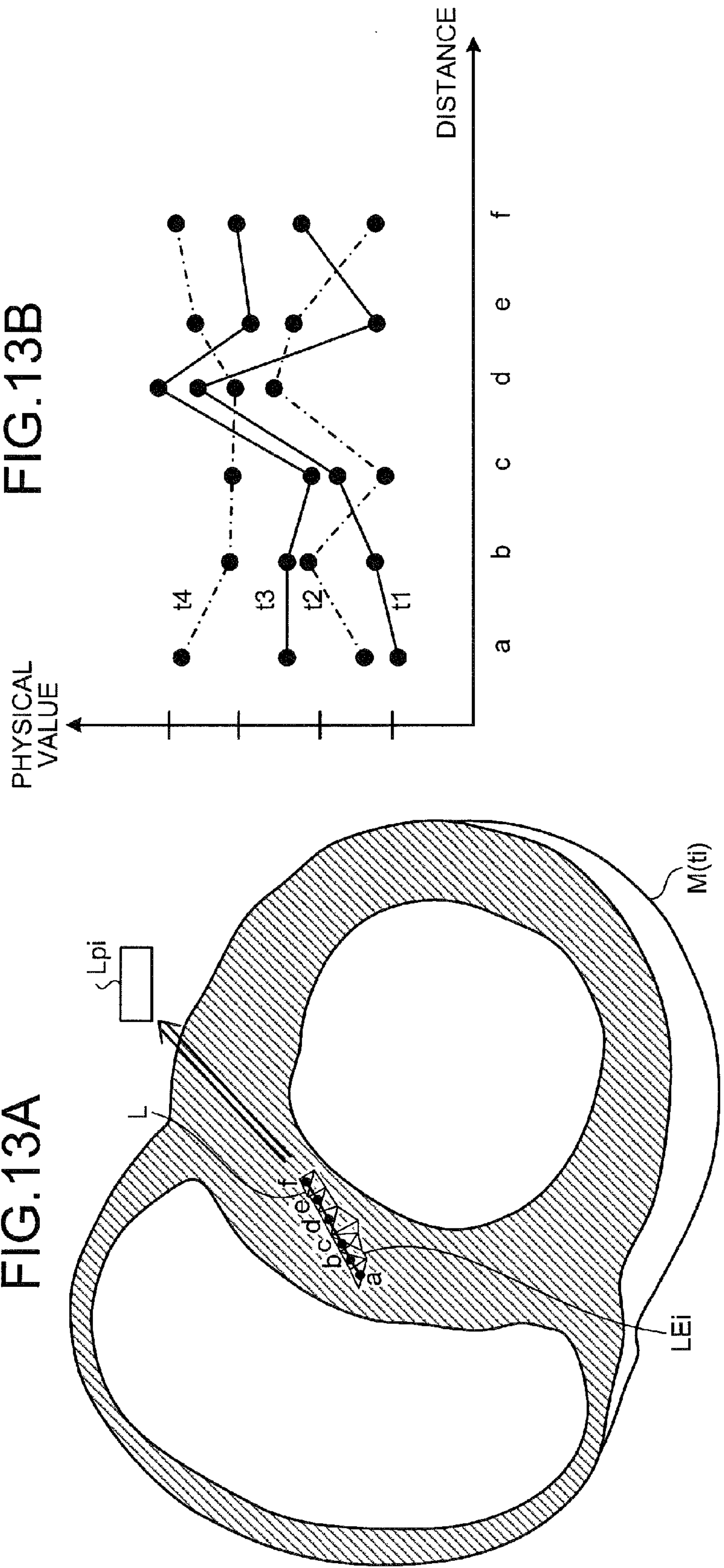
FIGS. 13A and 13B are diagrams depicting a behavior tracing example of the heart model according to a third embodiment.

FIGS. 13A and 13B are diagrams depicting a behavior tracing example of the heart model according to the third embodiment. Unlike the first embodiment, the line L1 in the heart model M(t1) at time t1 and the line L2 in the heart model M(t2) at time t2 are at the same position at times t1 and t2 in a 3-dimensional coordinate system.

In FIG. 13A, the display apparatus 500, via the specifying unit 502, specifies a line L in the heart model M(t1) at time t1. The specification/setting of the line L is performed only for the heart model M(t1). The display apparatus 500, via the detecting unit 503, detects a tetra element string LE1 that includes the line L. The respective tetra elements in the detected tetra element string LE1 are regarded as tetra elements_a to f. The display apparatus 500, via the extracting unit 505, extracts a physical value string Lp1 of the tetra element string LE1.

When the time changes from time t1 to time t2, the display apparatus 500 detects in the heart model M(t2), the tetra elements_a to f of the tetra element string LE1 obtained from the heart model M(t1). The display apparatus 500, via the extracting unit 505, extracts a physical value string Lp2 of the tetra element string LE2. Thus, each time the time changes, the display apparatus 500 detects the same tetra elements and extracts the physical value string thereof.

In FIG. 13B, the display apparatus 500, via the displaying unit 508, depicts a graph of the extracted physical value string Lpi. In FIG. 13B, the inter-element distances of tetra element string LEi are not reflected. Consequently, the display apparatus 500, via the displaying unit 508, displays the tetra element string LEi graphed at equal intervals. Nonetheless, configuration may be such that the display apparatus 500, via the calculating unit 504, calculates the inter-element distances and reflects the inter-element distances along the horizontal axis. Thus, in the third embodiment, the movement of the tetra elements_a to f making up the tetra element string LE1 that passes through the line L first specified, can be traced over time.

The functional configuration of the display apparatus 500 according to the third embodiment is, for example, identical to that depicted in FIG. 5. However, the detecting unit 503, upon detecting the tetra element string LE1 that passes through the line L specified by the specifying unit 502, detects at each changing of the time ti and in the heart model M(ti) at each time ti, the same tetra element group (tetra elements_a to f). Further, the setting unit 507, in the heart model M(ti) at time t2 and thereafter, sets a line at the same position and of the same length as the line L.

An example of the contents stored to the storage destination 510 by the storing unit 506 will be described. The storage destination 510 stores a tetra element string and an inter-element distance for each time ti. Description will be given with reference to FIGS. 14 and 15.

FIG. 14 is a diagram depicting an example of the data structures of the tetra element strings for each time ti. The storage destination 510 stores the data structures of tetra element strings LEi of the time step count n specified by the specifying unit 502. The tetra element name is a pointer to the data structure Di. Therefore, storage of the tetra element name enables the display apparatus 500 to extract from the data structure, the physical value of the tetra element specified by the tetra element name. For example, for tetra element E1(t1), specification of the tetra element name "E1(t1)" enables the display apparatus 500 to identify from the data structure D1, the physical value p(E1(t1)) of the tetra element E1(t1). Unlike the first and the second embodiments, at each time ti, the tetra element is the same element.

FIG. 15 is a diagram depicting an example of the data structures of the inter-element distance for each time ti. The storage destination 510 stores the data structures of inter-element distances of the time step count n specified by the specifying unit 502.

FIG. 16 is a flowchart of an example of the display process performed by the display apparatus 500 according to the third embodiment. The display apparatus 500, via the specifying unit 502, specifies the time step count n (step S1601), and sets the index i of time ti to be i=1 (step S1602). The display apparatus 500 specifies a line L in the heart model M(t1) at time t1 (step S1603).

The display apparatus 500, via the detecting unit 503, detects in the heart model M(t1), the tetra elements_a to f of the tetra element string LE1 that passes through the line L (step S1604). The display apparatus 500, via the calculating unit 504, calculates the inter-element distances (step S1605).

The display apparatus 500, via the extracting unit 505, extracts the physical value string Lpi from the tetra element string LEi (step S1606). The display apparatus 500, via the storing unit 506, correlates and stores the physical value string Lpi and the tetra element string LEi (step S1607). The display apparatus 500, via the storing unit 506 and for inter-element distances of the tetra element string LEi as well, correlates and stores the tetra element string LEi and the physical value string Lpi.

The display apparatus 500 increments the index i (step S1608). The display apparatus 500 determines whether i>n is true (step S1609). If i>n is not true (step S1609: NO), the display apparatus 500 sets a line identical to the line L (step S1610). The display apparatus 500, via the detecting unit 503, detects in a heart model M(ti) at time ti, a tetra element string LEi made up of the same elements_a to f as those in the tetra element string LE1 detected at step S1604 (step S1611), and returns to step S1605. Thus, at each time ti, steps S1605 to S1611 are executed. At step S1609, if i>n is true (step S1609: YES), the display apparatus 500, via the displaying unit 508, performs graphing and display (step S1612), whereby as depicted in FIG. 13B, a graph is displayed and a series of the operation according to the flowchart is ended.

Thus, in the third embodiment, the same tetra element string as the tetra element string that passes through the specified line can be traced over time. Therefore, the manner in which the tetra element string that passes through the specified line contracts and expands over time can be understood.

As described, according to the embodiments, tetra elements of both ends of a line are respectively the same elements at each time ti, whereby at each time ti, the tetra elements of both ends are fixed. Therefore, the varying movement of cardiac muscle over time and corresponding to the user-specified line can be traced.

Further, at each time ti, the line is evenly divided, whereby the element count of the tetra element string at each time to can be set to be identical. Therefore, the number of tetra elements to be traced is controlled, enabling faster display processing.

Further, a line is fixed irrespectively of the time ti, whereby movement of cardiac muscle corresponding to the line is traced by tetra element strings that pass through the line at each time ti. In other words, in a 3-dimensional space in which the heart model is arranged, although the heart model moves at each time ti, the line is present at the same position in the 3-dimensional space irrespective of the time ti. Therefore, the movement of cardiac muscle that over time, moves into the position of the user-specified line can be traced.

Further, by merely specifying a line in the heart model, the same tetra element string as the tetra element string that passes through the line can be traced over time. Therefore, the manner in which the tetra element string that passes through the specified line contracts and expands over time can be understood.

Thus, according to the embodiments, behavior of the interior of an internal organ can be easily traced.

All examples and conditional language provided herein are intended for pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. A non-transitory computer-readable recording medium that stores a display program for displaying simulation results and causing a computer to execute a process comprising:

detecting from a first element group included in a simulation model and having physical values according to a position in the simulation model of a first unit time, a first element string of elements along a first line that passes through the simulation model;

calculating first inter-element distances for elements of the first element string;

extracting from the first element string, first physical values of the elements of the first element string;

setting a second line that passes through the simulation model of a second unit time that is subsequent to the first unit time;

detecting from a second element group included in the simulation model and having physical values according to a position in the simulation model of the second unit time, a second element string that is along the second line and corresponds to the first element string;

calculating second inter-element distances for elements of the second element string;

extracting from the second element string, second physical values of elements of the second element string; and displaying the first physical values based on the calculated first inter-element distances and displaying the second physical values based on the calculated second inter-element distances.

2. The non-transitory computer-readable recording medium according to claim 1, wherein the setting includes identifying from the second element group of the second unit time, a starting-end element of the second unit time and a terminal-end element of the second unit time that are elements respectively identical to a starting-end element of the first unit time as a starting end of the first line and a terminal-end element of the first unit time as a terminal end of the first line, and setting the second line to connect the starting-end element of the second unit time and the terminal-end element of the second unit time.

3. The non-transitory computer-readable recording medium according to claim 2, wherein the detecting the first element string includes detecting from the first element group, the first element string that includes elements corresponding to the starting-end element of the first unit time, the terminal-end element of the first unit time, and division positions when the first line is divided evenly, and the detecting the second element string includes detecting from the second element group, the second element string that includes elements corresponding to the starting-end element of the second unit time, the terminal-end element of the second unit time, and division positions when the second line is divided evenly.

4. The non-transitory computer-readable recording medium according to claim 1, wherein the setting includes setting in the simulation model of the second unit time, the second line to be at a position identical to that of the first line.

5. The non-transitory computer-readable recording medium according to claim 1, and causing the computer to execute:

receiving from an input device, specification of the first line, wherein the detecting the first element string includes detecting from the first element group, the first element string that includes the specified first line.

6. A non-transitory computer-readable recording medium that stores a display program for displaying simulation results and causing a computer to execute a process comprising:

detecting from a first element group included in a simulation model and having physical values according to a position in the simulation model of a first unit time, a first element string of elements along a first line that passes through the simulation model;

calculating first inter-element distances for elements of the first element string;

extracting from the first element string, first physical values of the elements of the first element string;

setting a second line that passes through the simulation model of a second unit time that is subsequent to the first unit time;

detecting from a second element group included in the simulation model and having physical values according to a position in the simulation model of the second unit time, a second element string that is identical to the first element string and along the second line;

calculating second inter-element distances for elements of the second element string;

extracting from the second element string, second physical values of elements of the second element string; and displaying the first physical values based on the calculated first inter-element distances and displaying the second physical values based on the calculated second inter-element distances.

7. The non-transitory computer-readable recording medium according to claim 6, the process further comprising:

receiving from an input device, specification of the first line, wherein the detecting the first element string includes detecting from the first element group, the first element string that includes the first line.

8. A display method of displaying simulation results and executed by a computer, the display method comprising:

detecting from a first element group included in a simulation model and having physical values according to a position in the simulation model of a first unit time, a first element string of elements along a first line that passes through the simulation model;

calculating first inter-element distances for elements of the first element string;

extracting from the first element string, first physical values of the elements of the first element string;

setting a second line that passes through the simulation model of a second unit time that is subsequent to the first unit time;

detecting from a second element group included in the simulation model and having physical values according to a position in the simulation model of the second unit time, a second element string that is along the second line and corresponds to the first element string;

calculating second inter-element distances for elements of the second element string;

extracting from the second element string, second physical values of elements of the second element string; and displaying the first physical values based on the calculated first inter-element distances and displaying the second physical values based on the calculated second inter-element distances.

9. A display method of displaying simulation results and executed by a computer, the display method comprising:

detecting from a first element group included in a simulation model and having physical values according to a position in the simulation model of a first unit time, a first element string of elements along a first line that passes through the simulation model;

calculating first inter-element distances for elements of the first element string;

extracting from the first element string, first physical values of the elements of the first element string;

setting a second line that passes through the simulation model of a second unit time that is subsequent to the first unit time;

detecting from a second element group included in the simulation model and having physical values according to a position in the simulation model of the second unit time, a second element string that is identical to the first element string and along the second line;

calculating second inter-element distances for elements of the second element string;

extracting from the second element string, second physical values of elements of the second element string; and displaying the first physical values based on the calculated first inter-element distances and displaying the second physical values based on the calculated second inter-element distances.

10. A display apparatus that displays simulation results, the display apparatus comprising a computer configured to:

detect from a first element group included in a simulation model and having physical values according to a position in the simulation model of a first unit time, a first element string of elements along a first line that passes through the simulation model, calculate first inter-element distances for elements of the first element string, detect from a second element group included in the simulation model and having physical values according to a position in the simulation model of a second unit time that is subsequent to the first unit time, a second element string that corresponds to the first element string and is along a second line set to pass through the simulation model of the second unit time, and calculate second inter-element distances for elements of the second element string;

extract from the first element string, first physical values of the elements of the first element string, and extract from the second element string, second physical values of elements of the second element string; and display the first physical values based on the calculated first inter-element distances and display the second physical values based on the calculated second inter-element distances.

11. A display apparatus that displays simulation results, the display apparatus comprising a computer configured to:

detect from a first element group included in a simulation model and having physical values according to a position in the simulation model of a first unit time, a first element string of elements along a first line that passes through the simulation model, calculate first inter-element distances for elements of the first element string, detect from a second element group included in the simulation model and having physical values according to a position in the simulation model of a second unit time that is subsequent to the first unit time, a second element string that is identical to the first element string and along a second line, and calculate second inter-element distances for elements of the second element string;

extract from the first element string, first physical values of the elements of the first element string, and extract from the second element string, second physical values of elements of the second element string; and display the first physical values based on the calculated first inter-element distances and display the second physical values based on the calculated second inter-element distances.

* * * * *